US00PP18266P3

(12) United States Plant Patent
de Jong

(10) Patent No.: US PP18,266 P3
(45) Date of Patent: Dec. 4, 2007

(54) **VARIETY OF *HYDRANGEA* PLANT NAMED 'JON01'**

(50) Latin Name: ***Hydrangea* L. *macrophylla***
Varietal Denomination: JON01

(75) Inventor: Jos de Jong, Boskoop (NL)

(73) Assignee: De Jong Plant B.V., Boskoop (NL)

( * ) Notice: Subject to any disclaimer, the term of this patent is extended or adjusted under 35 U.S.C. 154(b) by 0 days.

(21) Appl. No.: 11/070,934

(22) Filed: Mar. 3, 2005

(65) Prior Publication Data

US 2006/0200881 P1 Sep. 7, 2006

(51) Int. Cl.
*A01H 5/00* (2006.01)

(52) U.S. Cl. ..... Plt./250
(58) Field of Classification Search ..... Plt./250
See application file for complete search history.

(56) References Cited

PUBLICATIONS

The New Royal Horticultural Society Dictionary of Gardening 1992 vol. 2 p. 606–611.*
UPOV–ROM Plant patent Variety Database 2005/05. Search for cultivar 'Lady in Red'.*

* cited by examiner

*Primary Examiner*—Kent Bell
*Assistant Examiner*—Annette H Para
(74) *Attorney, Agent, or Firm*—Fulwider Patton LLP

(57) ABSTRACT

A new and distinct cultivar of *hydrangea* plant named 'JON01' characterized by its distinctive color of flowers.

1 Drawing Sheet

BACKGROUND OF THE PLANT

The present invention relates to a new and distinct cultivar of *Hydrangea,* botanically known as *Hydrangea* L. *macrophylla* and further known by the varietal name 'JON01'. The plant is used primarily as an ornamental. The variety 'JON01' has been asexually reproduced by cuttings. The novel flower color was consistent through several generations, and plants remain true to type after multiple generations through asexual reproduction via cuttings. The new variety is a sport mutation of the variety 'Taube', discovered in the summer of 2001 by the breeder Jos de Jong in the breeder's nursery, Gebr. De Jong Handelskwekerijen BV in Boskoop, The Netherlands. The parental cultivar is sold under the Breeder's reference name "Taube."

SUMMARY OF THE INVENTION

The following traits have been repeatedly observed and are determined to be among the unique characteristics of 'JON01'. These characteristics distinguish 'JON01' as a new and distinct cultivar:

1. Different color of flowers, with the comparator (Taube) being dark pink to rosy-pink and this variety being dark rosy-red.

Plants of the cultivar 'JON01' have not been observed under all possible environmental and cultural conditions. The phenotype may vary somewhat with variations in environment such as temperature, light intensity, length of day, irrigation amount and frequency, and/or fertilizer rate without, however, any variance in genotype.

BRIEF DESCRIPTION OF THE DRAWINGS

The invention is depicted in the accompanying colored photographs in which.

Figure 1:
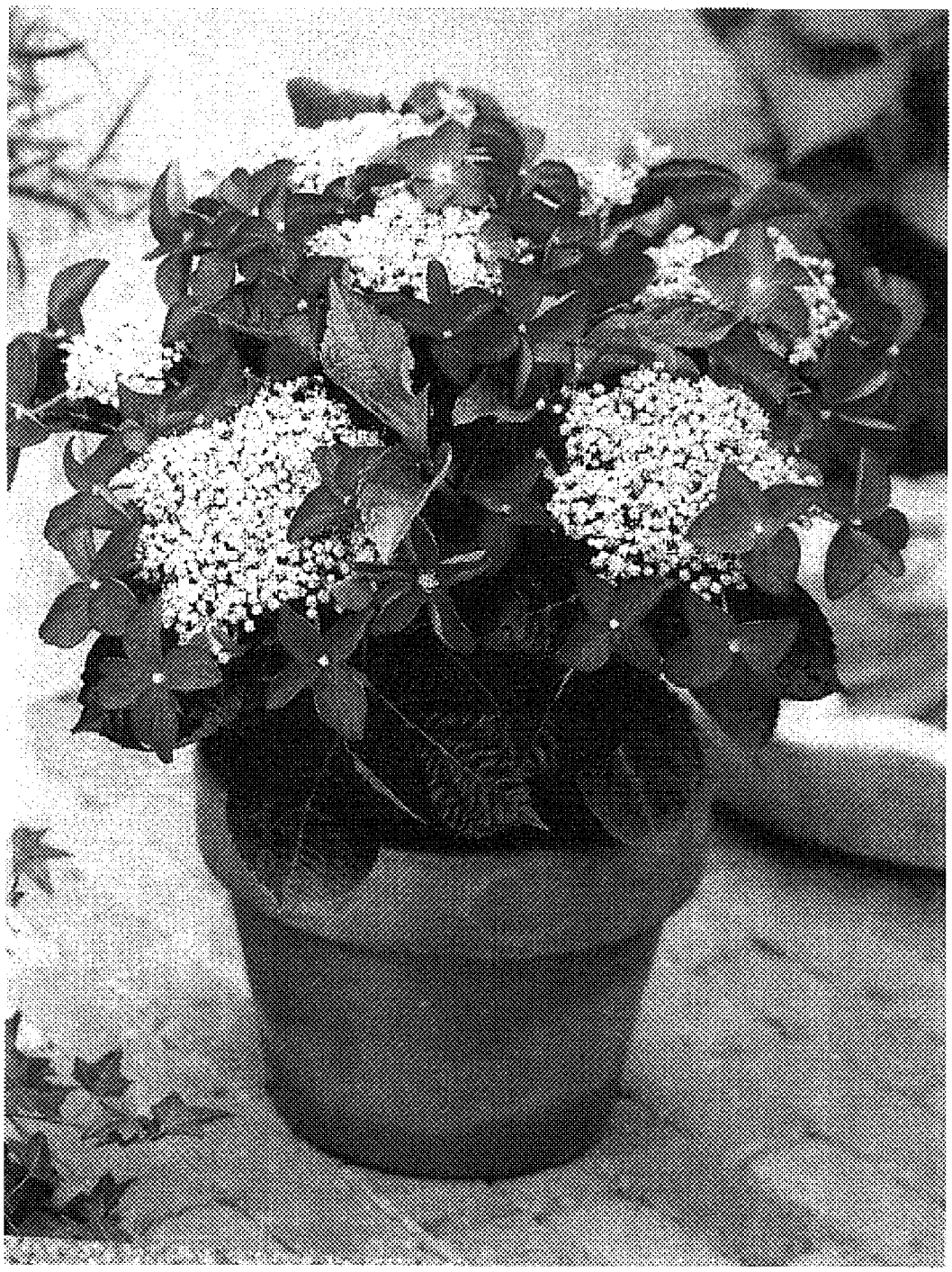
FIG. 1 shows a mature potted plant of the new variety.

The photograph depicts the overall appearance of the new *hydrangea* showing the colors as true as it is reasonably possible to obtain in colored reproductions of this type. Colors in the photographs may differ slightly from the color values cited in the Detailed Botanical Description, which more accurately describe the actual colors.

DETAILED BOTANICAL DESCRIPTION OF THE NEW PLANT

The following detailed description sets forth characteristics of the new cultivar.

| | |
|---|---|
| Botanical Name | *Hydrangea* L. *macrophylla* |
| Varietal Name | 'JON01' |
| Parentage: | Mutation of "Taube" |
| Asexual Propagation | Vegetatively by cuttings |
| Inflorescence: | |
| Color midzone upper surface - | 59B/60A (red-purple group); RHS 1995 |
| Fertile Flowers | star-shaped, diameter 7 mm, 4-6 petals; petal arrangement separated, color violet (RHS 85B, 1995) and white in a stripe pattern from base to apex, shape narrow cross section deep concave; pedicel length 2.2 mm, color pink |
| Sterile Flowers | round-shaped, diameter 50 mm, 4-6 petals, upper profile flat, lower profile slight concave; petal arrangement touching, color of upper side purplish red (RHS 71B, 1995), color of lower side purplish red (RHS 72D, 1995), shape rounded, basel spot absent; pedicel length 20 mm, color pink (RHS 72D, 1995) |

-continued

| | |
|---|---|
| Development: | |
| Resistance to Disease - | Similar to other *H. macrophylla* varieties; examined plants show no signs of pest or disease resistance or tolerance than other *hydrangea machrophylla* |
| Age and Growing Conditions | six first year plants raised in mulch beds, pH of 6.0, in full sun with some afternoon shade. Plants were of generally healthy appearance with some scorching and disfiguration from extremely hot conditions |
| Plant Size | |
| Plant Height | 300 mm |
| Plant Width | 250 mm |
| Habit | thick, rounded, branching arrangement irregular from leaf axil |
| Leaf Characteristics | |
| Length | 110-130 mm |
| Width | 82-90 mm |
| Vein | pattern prominent inset, cross section convex, undulation of margin slight |
| Color | Green upper side (RHS 137A, 1995), green lower side (RHS 137B, 1995), veins green (RHS 144B, 1995). |
| Petioles | |
| Texture | Smooth |
| Color | Green (RHS 144B, 1995) |
| Length | 13-18 mm |

-continued

| | |
|---|---|
| Stem | |
| Width | 5-8 mm |
| Texture | Smooth |
| Color | Green (RHS 144C, 1995), with some small burgundy/brown dots |
| Bud | |
| Shape | Round |
| Color | striped violet (RHS 85B, 1995) and white |
| Stamens | |
| Number of anthers | seven |
| Color of pollen | orange |
| Length | 1 mm |
| Pistil | |
| Number of pistils | three |
| Color | Yellow |
| Fruit | no fruit produced |
| Fragrance | very weak to absent, leaf fragrance weak to absent |

GENERAL CHARACTERISTICS

'JON01' is a mutation of the taube and differs from taube by the color of the flowers, with the comparator being dark pink to rosy pink and the present invention characterized by flowers being dark rosy-red.

What is claimed is:

1. A new and distinct variety of *hydrangea* plant, substantially as shown and described.

* * * * *